(12) United States Patent
Kimura (10) Patent No.: US 6,670,198 B2
(45) Date of Patent: Dec. 30, 2003

(54) TEST PIECE AND SYSTEM FOR READING OUT IMAGE INFORMATION FROM THE TEST PIECE

(75) Inventor: Toshihito Kimura, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/850,056

(22) Filed: May 8, 2001

(65) Prior Publication Data

US 2001/0024834 A1 Sep. 27, 2001

Related U.S. Application Data

(62) Division of application No. 09/572,886, filed on May 16, 2000, now Pat. No. 6,458,601.

(30) Foreign Application Priority Data

May 18, 1999 (JP) .............................. 11-137358

(51) Int. Cl.[7] ...................... G01N 33/53; G01N 33/543; G01N 33/00; C12M 3/00; C07H 21/00
(52) U.S. Cl. ...................... 436/518; 436/164; 436/501; 436/524; 436/528; 436/805; 435/6; 435/7.1; 435/7.2; 435/7.4; 435/7.5; 435/7.6; 435/7.7; 435/7.71; 435/7.72; 435/7.8; 435/7.9; 435/7.92; 435/91.1; 435/91.2; 435/174; 435/176; 435/177; 435/181; 435/287.1; 435/287.2; 435/287.8; 435/287.9; 435/288.3; 435/288.7; 435/808; 435/810; 435/969; 435/973; 422/68.1; 536/23.1; 536/24.1; 536/24.3; 536/24.31; 536/24.32; 536/24.33; 536/25.3

(58) Field of Search ................. 422/50, 68.1; 536/23.1, 536/24.1, 24.3, 24.31, 24.33, 25.3; 436/164, 172, 501, 518, 524, 528, 805; 435/6, 7.1, 7.2, 7.4, 7.5, 7.6, 7.7, 7.71, 7.72, 7.8, 7.9, 7.92, 91.1, 91.2, 174, 176, 177, 181, 287.1, 287.2, 287.8, 287.9, 288.3, 288.7, 808, 810, 969, 973

(56) References Cited

U.S. PATENT DOCUMENTS 4,728,591 A * 3/1988 Clark et al. .................. 430/5
5,143,854 A * 9/1992 Pirrung et al. ............... 436/518

(List continued on next page.)

FOREIGN PATENT DOCUMENTS

| EP | 0 814 593 A2 | * 12/1997 |
| EP | 0 814 594 A2 | * 12/1997 |
| JP | 10-003134 | 1/1998 |
| WO | WO 95/11454 A1 | * 4/1995 |

OTHER PUBLICATIONS

Larin et al. Fluorescence in situ hybridisation of multiple probes on a single microscope slide. Nucleic Acids Research (1994) vol. 22, No. 18, pp., 3689–3692.*

Guo et al. Direct Fluorescence analysis of genetic polymorphisms by hybridization with oligonucleotide arrays on glass supports. Nucleic Acids Research (1994) vol. 22, No. 24, pp. 5456–5465.*

Primary Examiner—Long V. Le
Assistant Examiner—Kartic Padmanabhan
(74) Attorney, Agent, or Firm—Sughrue Mion, PLLC (57) ABSTRACT

A test piece for use in biological analyses includes a plurality of different known specific binding substances disposed in predetermined positions on a substrate. The specific binding substances are disposed on a plurality of surfaces provided by the substrate and arranged in the direction of thickness of the substrate.

2 Claims, 4 Drawing Sheets

U.S. PATENT DOCUMENTS

| | | | |
|---|---|---|---|
| 5,168,157 A | * 12/1992 | Kimura | 250/234 |
| 5,252,719 A | * 10/1993 | Takeda et al. | 530/409 |
| 5,260,569 A | * 11/1993 | Kimura | 250/234 |
| 5,378,638 A | * 1/1995 | Deeg et al. | 436/518 |
| 5,445,934 A | * 8/1995 | Fodor et al. | 435/6 |
| 5,545,531 A | * 8/1996 | Rava et al. | 435/6 |
| 5,547,839 A | * 8/1996 | Dower et al. | 435/6 |
| 5,631,734 A | * 5/1997 | Stern et al. | 356/317 |
| 5,665,962 A | * 9/1997 | Kimura | 250/226 |
| 5,672,514 A | * 9/1997 | Tsuchiya et al. | 436/86 |
| 5,741,639 A | * 4/1998 | Ensing et al. | 435/6 |
| 5,800,992 A | * 9/1998 | Fodor et al. | 435/6 |
| 5,807,522 A | * 9/1998 | Brown et al. | 422/50 |
| 5,837,832 A | * 11/1998 | Chee et al. | 536/22.1 |
| 5,888,455 A | * 3/1999 | Seaton et al. | 422/63 |
| 5,900,640 A | * 5/1999 | Ogura | |
| 6,023,071 A | * 2/2000 | Ogura et al. | 250/586 |
| 6,037,186 A | * 3/2000 | Stimpson | 436/518 |
| 6,040,138 A | * 3/2000 | Lockhart et al. | 435/6 |
| 6,077,673 A | * 6/2000 | Chenchik et al. | 435/6 |
| 6,087,102 A | * 7/2000 | Chenchik et al. | 435/6 |
| 6,087,112 A | * 7/2000 | Dale | 435/6 |
| 6,129,896 A | * 10/2000 | Noonan et al. | 422/82.05 |
| 6,130,440 A | * 10/2000 | Ogura | 250/586 |
| 6,140,045 A | * 10/2000 | Wohlstadter et al. | 435/6 |
| 6,174,683 B1 | * 1/2001 | Hahn et al. | 435/6 |
| 6,255,476 B1 | * 7/2001 | Vinayak et al. | 536/25.32 |
| 6,391,562 B2 | * 5/2002 | Kambara et al. | 204/450 |

* cited by examiner

TEST PIECE AND SYSTEM FOR READING OUT IMAGE INFORMATION FROM THE TEST PIECE

This is a DIVISIONAL of application Ser. No. 09/572,886 filed May 16, 2000, the disclosure of which is incorporated herein by reference.

BACKGROUND OF THE INVENTION

1. Field of the Invention

This invention relates to a test piece for use in DNA analysis, immunological analysis, and the like, and a system for reading out image information from the test piece.

2. Description of the Related Art

Recently, genetic engineering has exhibited rapid progress, and the human genome project for decoding the base sequence of human genomes which amount to 100,000 in number is progressing.

Further, enzyme immunoassay, fluorescent antibody technique and the like utilizing antigen-antibody reactions have been used in diagnoses and studies, and studies for searching DNAs which affect genetic diseases are now progressing. In such a situation, a microarray technique is now attracting attention.

In the microarray technique, a microarray chip (sometimes called a DNA chip) comprising a plurality of known cDNAs (an example of specific binding substances) coated in a matrix on a substrate such as a membrane filter or a slide glass at a high density (at intervals of not larger than several hundred $\mu$m) is used and DNAs (an example of organism-originating substances) taken from cells of a normal person A and labeled with a fluorescent dye a and DNAs taken from cells of a genetic-diseased person B and labeled with a fluorescent dye b are dropped onto the microarray chip by pipettes or the like, thereby hybridizing the DNAs of the specimens with the cDNAs on the microarray chip. Thereafter, exciting light beams which respectively excite the fluorescent dyes a and b are projected onto the cDNAs by causing the exciting light beams to scan the microarray chip and fluorescence emitted from each other of the cDNAs is detected by a photodetector. Then the cDNAs with which the DNAs of each specimen are hybridized are determined on the basis of the result of the detection, and the cDNAs with which the DNAs of the normal person A are hybridized and those with which the DNAs of the diseased person B are hybridized are compared, whereby DNAs expressed or lost by genetic disease can be determined.

In the microarray technique, it is necessary to precisely two-dimensionally scan the microarray chip coated with cDNAs at a high density, and there has been proposed a radiation image read-out apparatus with such a precise scanning system. See, for instance, Japanese Unexamined Patent Publication No. 10(1998)-3134.

The kinds of cDNAs to be used sometimes amount to several tens of thousands and in such a case, the cDNAs must be coated on a plurality of substrates. However when the number of the microarray chips to be used increases, replacement of microarray chips becomes troublesome.

SUMMARY OF THE INVENTION

In view of the foregoing observations and description, the primary object of the present invention is to provide a test piece on which an increased number of specific binding substances such as cDNAs can be disposed, and a system for reading out image information from the test piece.

In accordance with one aspect of the present invention, there is provided a test piece such as a microarray chip for use in biological analyses comprising a plurality of different known specific binding substances such as cDNAs disposed in predetermined positions on a substrate such as a slide glass, wherein the improvement comprises that the specific binding substances are disposed on a plurality of surfaces provided by the substrate and arranged in the direction of thickness of the substrate.

The plurality of surfaces provided by the substrate and arranged in the direction of thickness of the substrate may be opposite sides of the substrate or may be provided by a multi-layered substrate formed by a plurality of substrates which are stacked and bonded together so that the surfaces on which the specific binding substances are disposed are substantially in parallel to each other.

It is preferred that the specific binding substances be disposed on the surfaces in positions where the specific binding substances on the respective surfaces do not interfere with each other in the direction of thickness of the substrate, that is, the specific binding substances on the respective surfaces do not overlap with each other in the direction of thickness of the substrate.

The substrate may be formed of any material so long as the specific binding substances can be spotted and stably held on the substrate and the substrate is optically transparent to the exciting light and the fluorescence emitted from the specific binding substances upon exposure to the exciting light. For example, the substrate may be a membrane filter or a slide glass. Further the substrate may be subjected to pretreatment so that the specific binding substances are stably held on the substrate.

The specific binding substances include hormones, tumor markers, enzymes, antibodies, antigens, abzymes, other proteins, nucleic acids, cDNAs, DNAs, RNAs, and the like, and means those which can be specifically bound with an organism-originating substance. The means of the expression "known" differs by the specific binding substance. For example, when the specific binding substance is a nucleic acid, "known" means that the base sequence, the lengths of the bases and the like are known, and when specific binding substance is protein, "known" means that the composition of the amino acid is known. The specific binding substances are disposed by one kind for each position.

In accordance with another aspect of the present invention, there is provided a system for reading out image information from the test piece of the present invention comprising a test piece holder portion which holds a test piece of the present invention the specific binding substances on which have been hybridized with an organism-originating substance labeled with fluorescent dye, an exciting light source which emits exciting light for exciting the fluorescent dye, a photoelectric read-out means which photoelectrically reads out fluorescence emitted from the fluorescent dye upon exposure to the exciting light, a scanning means which has an optical head for projecting the exciting light onto the test piece and leading fluorescence, which is emitted from the fluorescent dye and travels through the surface of the test piece onto which the exciting light is projected, to the photoelectric read-out means, and causes the exciting light to scan the test piece, and a controller which controls the exciting light source, the photoelectric read-out means and the scanning means so that fluorescence emitted from the specific binding substances upon exposure to the exciting light is detected for each of the surfaces of the test piece.

The test piece holder portion may comprise a table on which the test piece is placed. In this case, the test piece is placed on the table with its one side in contact with the table, and accordingly, it is necessary that the table is transparent to at least the fluorescence. When the test piece holder portion is in the form of a member which supports only the four corners of the test piece, the test piece holder portion need not be transparent.

The organism-originating substance may be a wide variety of substances originated from an organism including hormones, tumor markers, enzymes, proteins, antibodies, various substances which can be antigens, nucleic acids, cDNAs, mRNAs and the like.

The exciting light is light suitable for exciting the fluorescent dye including a laser beam.

As the photoelectric read-out means, a photomultiplier which can detect at a high sensitivity weak light such as fluorescence may be suitably used. However, various known photoelectric read-out means such as a cooled CCD may be used without limited to the photomultiplier.

In accordance with the present invention, since the specific binding substances are disposed on a plurality of surfaces provided by the substrate and arranged in the direction of thickness of the substrate, an increased number of specific binding substances can be disposed on one test piece and accordingly, the number of test pieces to be used can be less even if a large number of specific binding substances are used, whereby the frequency at which the test pieces are replaced can be reduced and reading operation can be effectively performed.

When the specific binding substances are disposed on opposite sides of a single substrate, the test piece can be manufactured at low cost.

DESCRIPTION OF THE PREFERRED EMBODIMENTS

Figure 1:
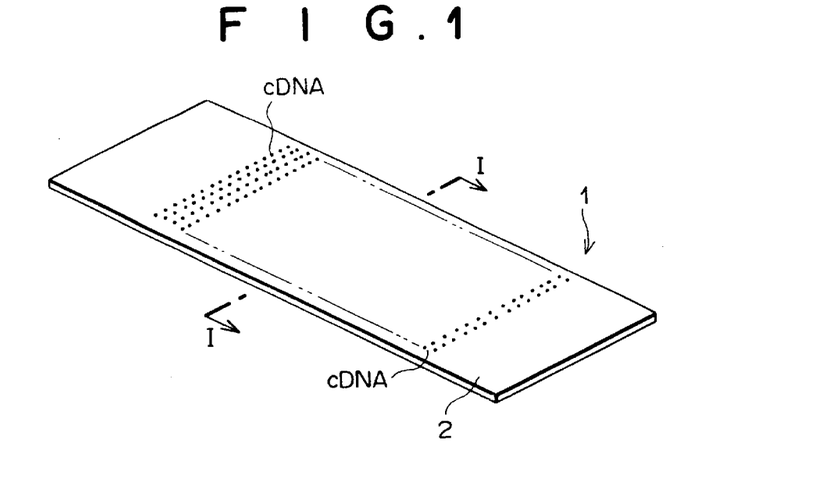
FIG. 1 is a perspective view of a test piece in accordance with a first embodiment of the present invention.
Figure 2:
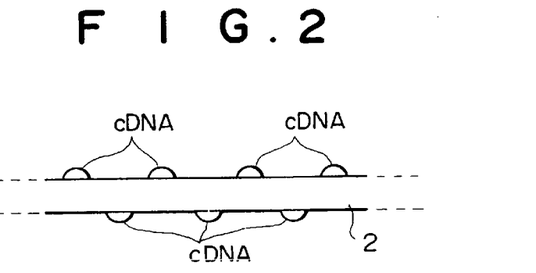
FIG. 2 is a cross-sectional view taken along line I—I in FIG. 1.

In FIGS. 1 and 2, a test piece 1 in accordance with a first embodiment of the present invention comprises a substrate 2 which is a slide glass in this particular embodiment, and a plurality of different cDNAs disposed in a plurality of positions on opposite sides (upper and lower sides) of the substrate 2. The base sequences of the cDNAs are known and correspond to different DNAs. The kind of each cDNA and the position of each cDNA are predetermined.

As shown in FIG. 2, the cDNAs on the upper side of the substrate 2 and those on the lower side of the substrate 2 are positioned not to overlap each other in the direction of thickness of the substrate 2. Further the upper and lower sides of the substrate 2 have been subjected to surface treatment so that the cDNAs are bonded to the surfaces and accordingly, the cDNAs on the lower side of the substrate 2 cannot peel off the substrate 2. The thickness of the substrate 2 is about 1 mm, and each of the cDNAs is disposed on the surface of the substrate 2 in a spot of a diameter 30 to 100 $\mu$m with the spot intervals of about 300 $\mu$m.

Figure 3:
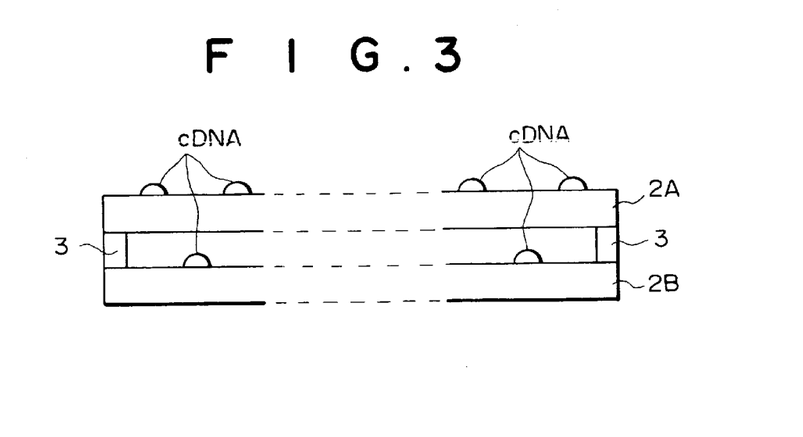
FIG. 3 is a cross-sectional view of a test piece in accordance with a second embodiment of the present invention.

FIG. 3 shows a test piece in accordance with a second embodiment of the present invention. The test piece shown in FIG. 3 is provided with a substrate formed of a pair of substrate segments 2A and 2B which are bonded together with a spacer 3 interposed therebetween. The cDNAs are disposed on the upper surfaces of the respective substrate segments 2A and 2B not to overlap each other in the direction of thickness of the substrate segments 2A and 2B. The spacer 3 may either be discontinuous or continuous over the entire periphery of the substrate segments 2A and 2B.

Figure 4A:
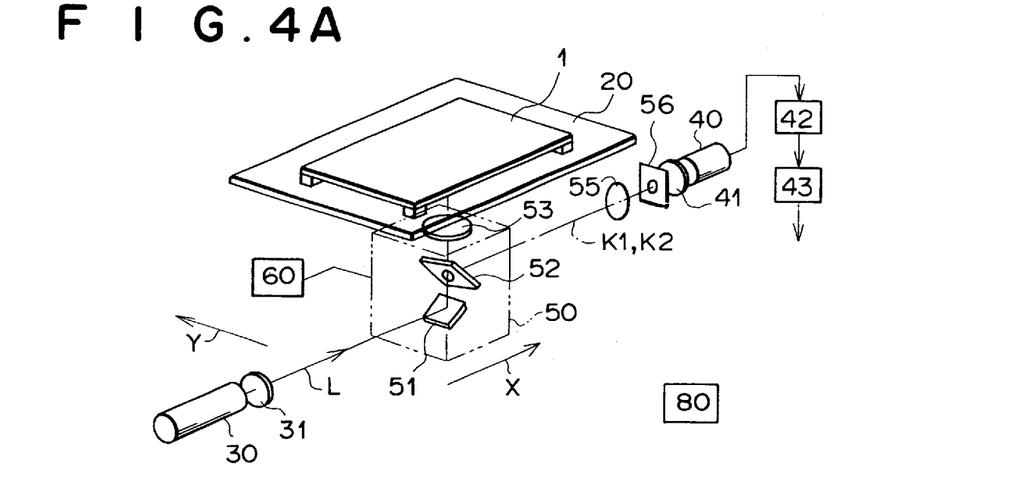
FIG. 4A is a perspective view of an image information read-out system in accordance with a third embodiment of the present invention.
Figure 4B:
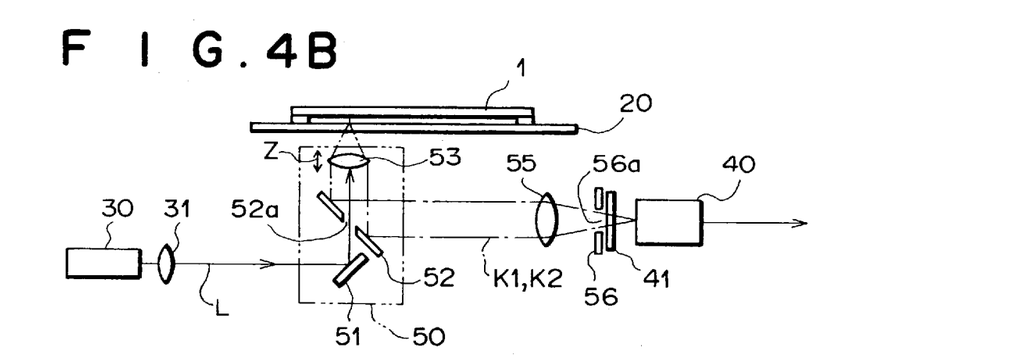
FIG. 4B is a schematic side view of the image information read-out system.

FIGS. 4A and 4B show an image information read-out system in accordance with a third embodiment of the present invention for reading out image information from the test piece 1 shown in FIG. 1. The image information read-out system comprises a transparent sample table 20 on which the test piece 1, having applied with an organism-originating substance labeled with a fluorescent dye, is supported at its four corners, a laser 30 which emits a laser beam L in a wavelength band exciting the fluorescent dye, a lens 31 which converges the laser beam L as emitted from the laser 30 into a thin laser beam, a photomultiplier 40 which photoelectrically detects fluorescence K1 and K2 emitted from the cDNAs upon exposure to the laser beam L (K1 represents the fluorescence emitted from the cDNAs on the upper surface of the substrate 2 and K2 represents the fluorescence emitted from the cDNAs on the lower surface of the substrate 2), an optical head 50 which causes the laser beam L to impinge upon the test piece 1 on the sample table 20 and leads the fluorescence K1 or K2 to the photomultiplier 40, a laser beam cut filter 41 disposed on the optical path between the optical head 50 and the photomultiplier 40, a condenser lens 55 which is disposed between the test piece 1 and the photomultiplier 40 and forms a confocal optical system together with a lens 53, an aperture plate 56 which has an aperture 56a which permits to impinge upon the lens 41 only light from a portion of the test piece 1 on which the laser beam L is converged by the lens 53, a main scanning system 60 which moves the optical head 50 in the direction of arrow X at a constant speed, a sub-scanning means 80 which moves the laser 30, the optical head 50, the condenser lens 55, the aperture plate 56, the laser beam cut filter 41 and the photomultiplier 40 in the direction of arrow Y (perpendicular to the direction of arrow X) integrally with each other, a logarithmic amplifier 42 which logarithmically amplifies a detecting signal output from the photomultiplier 40, and an A/D converter 43 which digitizes the amplified detecting signal.

The laser 30 is arranged to emits the laser beam L in the direction of arrow X, and the photomultiplier 40 is arranged to detect the fluorescence K1 or K2 impinging thereupon in the direction of arrow X.

The optical head 50 comprises a plane mirror 51 which reflects the thin laser beam L, traveling in the direction of arrow X, in a direction perpendicular to the surfaces of the test piece 1, a mirror 52 which is provided with an aperture 52a through which the laser beam L reflected by the plane mirror 51 impinges upon the test piece 1 and reflects the major parts of the fluorescence K1 or K2, emitted downward from the lower surface of the test piece 1, to impinge upon the photomultiplier 40, and the lens 53 which collimates the fluorescence K1 or K2 which emits downward from the test piece 1 as divergent light. The plane mirror 51, the mirror 52 with the aperture 52a and the lens 53 are integrated into a unit. The lens 53 is movable in the direction of thickness of the test piece 1 or in the direction of arrow z to move a focal point of the lens 53 selectively to the upper surface of the substrate 2 and to the lower surface of the same. When the fluorescence K1 from the upper surface of the test piece 1 is to be detected, the focal point of the lens 53 is moved to the upper surface of the test piece 1 and when the fluorescence K2 from the lower surface of the test piece 1 is to be detected, the focal point of the lens 53 is moved to the lower surface of the test piece 1, whereby the florescence K1 and K2 can be collimated to beams of substantially the same diameters.

The laser beam cut filter 41 is a filter which transmits the fluorescence K1 and K2 but does not transmit the laser beam L so that a part of the laser beam L scattered by the test piece 1, the sample table 20 and the like cannot impinge upon the photomultiplier 40.

Operation of the image information read-out system of this embodiment will be described, hereinbelow.

The position of the lens 53 is first adjusted so that the focal point of the lens 53 is on the upper surface of the substrate 2. Then the main scanning means 60 moves the optical head 50 at a constant high speed in the direction of arrow X. At each moment during movement of the optical head 50, the laser 30 emits a laser beam L in the direction of arrow X and the lens 31 converges the laser beam L into a thin laser beam. The thin laser beam L enters the optical head 50. The laser beam L is then reflected upward by the plane mirror 51 and impinges upon a fine area on the upper surface of the test piece 1 through the aperture 52a of the mirror 52 and the lens 53.

When an organism-originating substance labeled with fluorescent dye exists in the fine area exposed to the laser beam L, the fluorescent dye is excited by the laser beam L and emits fluorescence K1.

The fluorescence K1 spread around the area and the part of the fluorescence K1 traveling downward from the lower surface of the test piece 1 is collimated by the lens 53 of the optical head 50 into a substantially parallel downward beam and impinges upon the mirror 52. Though the part of the fluorescence K1 impinges upon the aperture 52a travels further downward through the aperture 52a (the diameter of the aperture 52a is sufficiently small as compared with the beam diameter), the major part of the fluorescence K1 is reflected by the mirror 52 to travel in the direction of arrow X and to impinge upon the photomultiplier 40 through the condenser lens 55, the aperture 56a of the aperture plate 56 and the laser bean cut filter 41.

Though a part of the laser beam L impinging upon the test piece 1 is scattered by the test piece 1, the sample table 20 and the like and travels toward the photomultiplier 40, it is prevented from impinging upon the photomultiplier 40 by the laser beam cut filter 41. Further since the test piece 1 and the photomultiplier 40 are optically connected by a confocal optical system, fluorescence from a part of the test piece other than the part exposed to the laser beam L is prevented from impinging upon the photomultiplier 40 and blur of a fluoresce image obtained can be avoided even if the area exposed to the laser beam L is shifted or enlarged.

The fluorescence K1 impinging upon the photomultiplier 40 is photoelectrically detected by the photomultiplier 40 and read out as an electric signal. The electric signal is amplified by the amplifier 42 and is converted to a digital signal by the A/D converter 43.

During these steps, the optical head 50 is kept moved in the direction of arrow X by the main scanning system 60, and a digital signal is output from the A/D converter 43 for each main scanning position on the test piece 1.

Each time the main scanning along one line is ended, the sub-scanning means 80 slightly moves the laser 30, the optical head 50, the laser beam cut filter 41 and the photomultiplier 40 in the direction of arrow Y (sub-scanning) and the main scanning is repeated. The sub-scanning may be effected in parallel to the main scanning.

Thus the entire area of the upper surface of the test piece 1 is two-dimensionally scanned by the laser beam L, and image information representing the distribution of the organism-originating substances labeled by the fluorescent dye on the upper surface of the substrate 2 is obtained.

Figure 5:
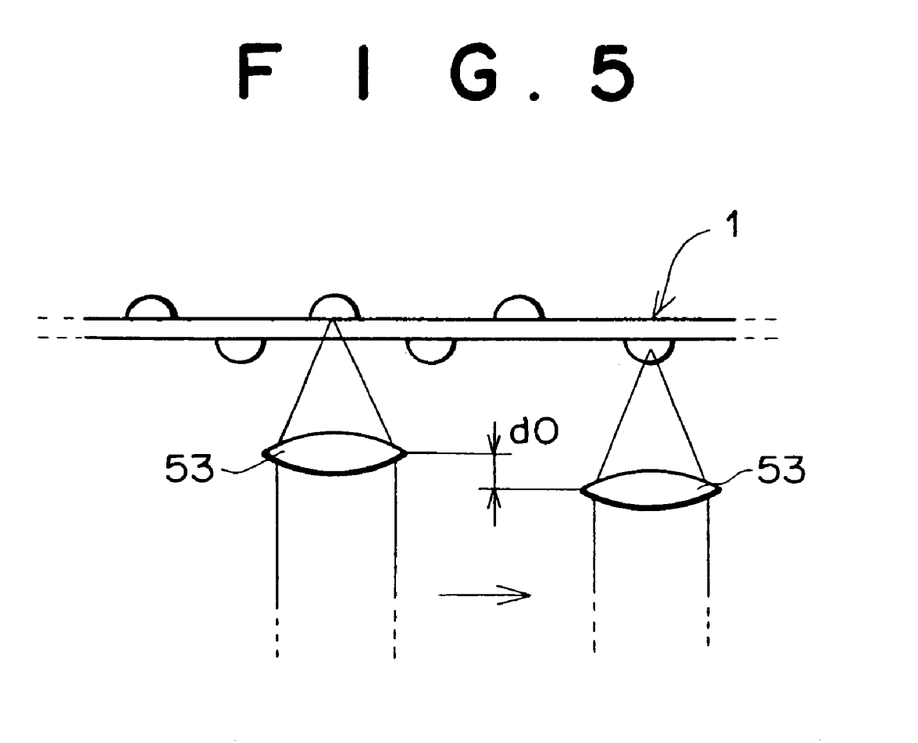
FIG. 5 is a view for illustrating the operation of the image information read-out system of the third embodiment.

Thereafter the optical head 50 is returned to the initial position by the main scanning means 60 and the sub-scanning means 80. Then the lens 53 is moved downward by d0 (FIG. 5) so that the focal point of the lens 53 is on the lower surface of the substrate 2. Then the fluorescence K2 emitted from the lower surface of the test piece 1 is detected and converted to a digital signal in the same manner as described above and image information representing the distribution of the organism-originating substances labeled by the fluorescent dye on the lower surface of the substrate 2 is obtained.

The image information representing the distribution of the organism-originating substances labeled by the fluorescent dye on the upper and lower surfaces of the substrate 2 is displayed on a monitor (not shown).

Thus in the image information read-out system of this embodiment, image information can be read out from opposite sides of the test piece 1 of the first embodiment of the present invention, where cDNAs are disposed on opposite sides of the substrate 2.

The image information read-out system of this embodiment can be used to read out image information from the test piece of the second embodiment of the present invention shown in FIG. 3. In this case, the lens 53 is moved so that the focal point of the lens 53 is selectively moved to the upper surface of the substrate segment 2A and that of the substrate segment 2B.

Though, in the embodiment described above, the fluorescence K1 emitted from the cDNAs on the upper surface of the substrate 2 and the fluorescence K2 emitted from the cDNAs on the lower surface of the substrate 2 are separately detected by moving the focal point of the lens 53 forming a confocal optical system, it is possible to separately detect the fluorescence K1 and the fluorescence K2 by moving the aperture plate 56 along the optical axis with the lens 53 kept stationary. That is, when the laser beam L is projected onto the test piece 1 with the focal point of the lens 53 set at the middle between the upper and lower surfaces of the substrate 2, the fluorescence K1 is emitted from the cDNAs on the upper surface of the substrate 2 and the fluorescence K2 is emitted from the cDNAs on the lower surface of the substrate 2. Depending on the position of the aperture plate 56 along the optical axis, only one of the fluorescence K1 and the fluorescence K2 can pass through the aperture 56a in the aperture plate 56.

Figure 6A:
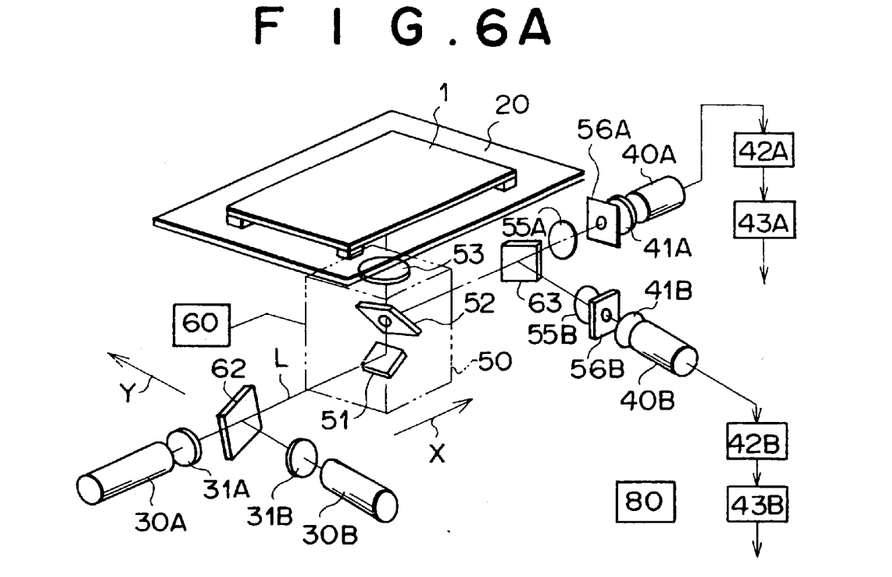
FIG. 6A is a perspective view of an image information read-out system in accordance with a fourth embodiment of the present invention.
Figure 6B:
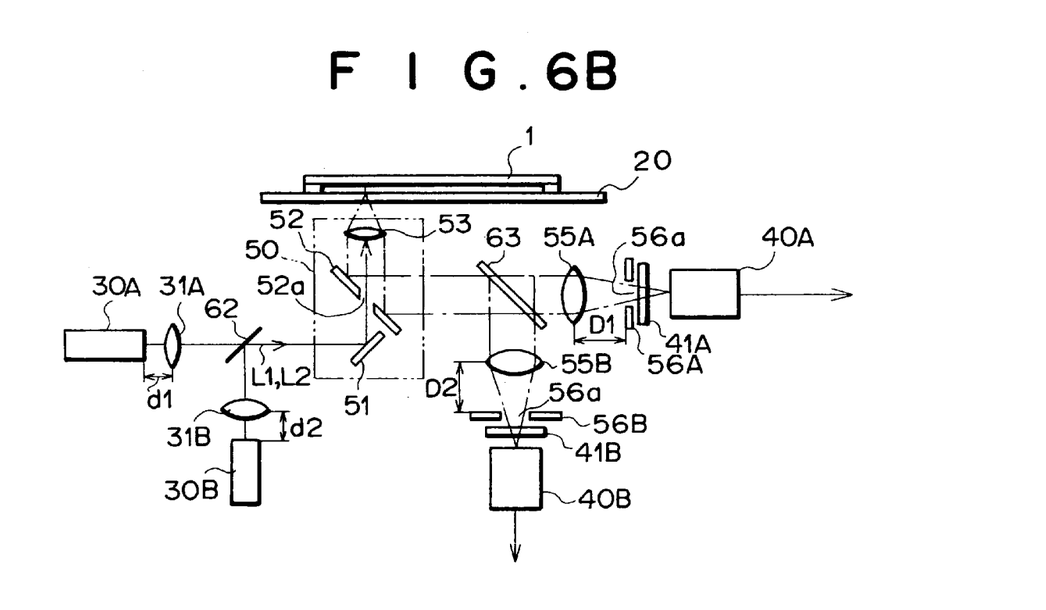
FIG. 6B is a schematic side view of the image information read-out system.

FIGS. 6A and 6B show an image information read-out system in accordance with a fourth embodiment of the present invention for reading out image information from the test piece 1 shown in FIG. 1. The image information read-out system of this embodiment comprises a sample table 20, a first laser 30A, a first lens 31A, a first photomultiplier 40A, an optical head 50, a first laser beam cut filter 41A, a first condenser lens 55A, a first aperture plate 56A, a main scanning system 60, a sub-scanning means 80, a first logarithmic amplifier 42A, and a first A/D converter 43A, which are basically the same as the sample table 20, the laser 30, the lens 31, the photomultiplier 40, the optical head 50, the laser beam cut filter 41, the condenser lens 55, the aperture plate 56, the main scanning system 60, the sub-scanning means 80, the logarithmic amplifier 42, and the A/D converter 43 employed in the third embodiment. The image information read-out system of this embodiment further comprises a second laser 30B, a second lens 31B, a second condenser lens 55B, a second aperture plate 56B, a second laser beam cut filter 41B, a second photomultiplier 40B, a second logarithmic amplifier 42B, a second A/D converter 43B, a polarization beam splitter 62 which transmits the laser beam L1 emitted from the first laser 30A and reflects the laser beam L2 emitted from the second laser 30B, and a half-silvered mirror 63 which transmits a part of the fluorescence K1 and the fluorescence K2 to impinge upon the first photomultiplier 40A, and reflects the other part of the fluorescence K1 and the fluorescence K2 to impinge upon the second photomultiplier 40B.

The first and second lenses 31A and 31B are identical to each other. The first and second lasers 30A and 30B are basically identical to each other except that the laser beam L1 emitted from the first laser 30A is polarized in the vertical direction as seen in FIG. 6B and the laser beam L2 emitted from the second laser 30B is polarized in a direction perpendicular to the surface of the paper on which FIG. 6B is drawn. With this arrangement, the laser beam L1 transmits the polarization beam splitter 62 and the laser beam L2 is reflected by the same.

The distance d2 between the beam radiating end of the second laser 30B and the second lens 31B is set larger than the distance d1 between the beam radiating end of the first laser 30A and the first lens 31A so that the diameter of the laser beam L1 on the upper surface of the substrate 2 becomes equal to the diameter of the laser beam L2 on the lower surface of the substrate 2.

Further, the distance D2 between the second condenser lens 55B and the second aperture plate 56B is set larger than the distance D1 between the first condenser lens 55A and the first aperture plate 56A. In the fourth embodiment, the leaser beams L1 and L2 are simultaneously emitted from the first and second lasers 30A and 30B, and the fluorescence K1 and the fluorescence K2 emitted respectively from the upper and lower surfaces of the test piece 1 are simultaneously detected. The fluorescence K1 and the fluorescence K2 emitted respectively from the upper and lower surfaces of the test piece 1 simultaneously travel in the direction of arrow X. The fluorescence K1 and the fluorescence K2 emitted respectively from the upper and lower surfaces of the test piece 1 are separated by the half-silvered mirror 63 to parts which respectively travel to the first and second photomultipliers 40A and 40B. Either of the parts includes both the fluorescence K1 and the fluorescence K2, and accordingly, the distance D2 between the second condenser lens 55B and the second aperture plate 56B is set larger than the distance D1 between the first condenser lens 55A and the first aperture plate 56 so that only the fluorescence K1 can pass through the aperture of the first aperture plate 56A and only the fluorescence K2 can pass through the aperture of the second aperture plate 56B, whereby the fluorescence K1 and the fluorescence K2 are separately detected by the photomultipliers 40A and 40B, respectively.

Operation of the image information read-out system of this embodiment will be described, hereinbelow.

When the laser beams L1 and L2 are projected onto the upper and lower surfaces of the test piece 1, fluorescence K1 and fluorescence K2 are emitted from the upper and lower surfaces of the test piece 1, respectively, and simultaneously travel in the direction of arrow X as a light bundle. The light bundle is divided into two light bundles by the half-silvered mirror 63, one traveling toward the first photomultiplier 40A and the other traveling toward the second photomultiplier 40B. The fluorescence K1 included in said one light bundle impinges upon the first photomultiplier 40A through the first condenser lens 55A, the first aperture plate 56A and the first laser beam cut filter 41A and is detected by the first photomultiplier 40A, whereas the fluorescence K2 included in said the other light bundle impinges upon the second photomultiplier 40B through the second condenser lens 55B, the second aperture plate 56B and the second laser beam cut filter 41B and is detected by the second photomultiplier 40B.

The fluorescence K1 and the fluorescence K2 are photoelectrically converted to electric signals respectively by the first and second photomultipliers 40A and 40B, and the electric signals are amplified by the first and second amplifiers 42A and 42B and then digitized by the first and second A/D converters 43A and 43B. Then visible images are displayed on a monitor (not shown) on the basis of the digitized electric signals.

Thus also in the image information read-out system of this embodiment, image information can be read out from opposite sides of the test piece 1 of the first embodiment of the present invention, where cDNAs are disposed on opposite sides of the substrate 2.

The image information read-out system of this embodiment can be used to read out image information from the test piece of the second embodiment of the present invention shown in FIG. 3. In this case, positions of the first and second lenses 31A and 31B and the first and second aperture plates 56A and 56B are adjusted to read out image information from the substrate segments 2A and 2B.

Though, in the embodiments described above, the cDNAs are disposed not to overlap each other in the direction of thickness of the substrate 2 or the substrate segments 2A and 2B, they may overlap each other in the direction of thickness of the substrate 2 or the substrate segments 2A and 2B when the image information read-out system comprises a confocal optical system.

What is claimed is:

1. An image information read-out system, comprising:
   a test piece holder portion which holds a test piece having specific binding substances which have been hybridized with an organism-originating substance labeled with fluorescent dye, the specific binding substances being disposed on a plurality of surfaces of the test piece;
   an exciting light source which emits exciting light for exciting the fluorescent dye;
   photoelectric read-out means which photoelectrically reads out fluorescence emitted from the fluorescent dye upon exposure to the exciting light;

scanning means which has an optical head for projecting the exciting light onto the test piece, for leading fluorescence, which is emitted from the fluorescent dye and travels back towards the exciting light being projected onto the test piece, to the photoelectric read-out means, and for causing the exciting light to scan the test piece; and a controller which controls the exciting light source, the photoelectric read-out means, and the scanning means so that fluorescence, emitted from the specific binding substances upon exposure to the exciting light, is detected for each of the plurality of surfaces of the test piece wherein the plurality of surfaces are arranged in a direction of thickness of a substrate of the test piece, and wherein the specific binding substances are positioned such that they do not interfere with each other.

2. An image information read-out system, comprising:

a test piece holder which holds a test piece having a plurality of surfaces on which are provided specific binding substances which have been hybridized with an organism-originating substance labeled with fluorescent dye;

an exciting light source which emits exciting light for exciting the fluorescent dye;

a photodetector operative to photoelectrically read out fluorescence emitted from the fluorescent dye upon exposure to the exciting light;

an optical head operative to project the exciting light onto the test piece, to direct fluorescence, which is emitted from the fluorescent dye and which travels back towards the exciting light being projected onto the test piece, to the photodetector, and to cause the exciting light to scan the test piece; and a controller operative to control the exciting light source, the photodetector, and the optical head so that fluorescence, emitted from the specific binding substances upon exposure to the exciting light, is detected for each of a plurality of surfaces of the test piece wherein the plurality of surfaces are arranged in a direction of thickness of a substrate of the test piece, and wherein the specific binding substances are positioned such that they do not interfere with each other.

* * * * *